(12) United States Patent
Jain et al.

(10) Patent No.: US 10,145,776 B2
(45) Date of Patent: Dec. 4, 2018

(54) FLUID ANALYSIS USING DIGITAL IMAGERY

(71) Applicant: Massachusetts Institute of Technology, Cambridge, MA (US)

(72) Inventors: Pranay Jain, Delhi (IN); Sanjay E. Sarma, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/302,328

(22) PCT Filed: Apr. 12, 2016

(86) PCT No.: PCT/US2016/027070
§ 371 (c)(1),
(2) Date: Oct. 6, 2016

(87) PCT Pub. No.: WO2016/168167
PCT Pub. Date: Oct. 20, 2016

(65) Prior Publication Data
US 2017/0131197 A1 May 11, 2017

Related U.S. Application Data

(60) Provisional application No. 62/197,126, filed on Jul. 27, 2015, provisional application No. 62/146,456, filed on Apr. 13, 2015.

(51) Int. Cl.
*G01N 15/02* (2006.01)
*G01N 15/06* (2006.01)
(Continued)

(52) U.S. Cl.
CPC ......... *G01N 15/0227* (2013.01); *G01N 15/06* (2013.01); *G01N 21/51* (2013.01);
(Continued)

(58) Field of Classification Search
CPC .... G01N 15/0227; G01N 15/06; G01N 33/06; G01N 33/14; G01N 2015/03;
(Continued)

(56) References Cited

U.S. PATENT DOCUMENTS

| 4,672,457 A | 6/1987 | Hyatt |
| 6,020,588 A | 2/2000 | Ditmarsen et al. |

(Continued)

FOREIGN PATENT DOCUMENTS

| WO | WO 96/31764 | 10/1996 |
| WO | WO 2014/153047 | 9/2014 |

OTHER PUBLICATIONS

Pranay Jain and Sanjay E. Sarma, "Light scattering and transmission measurement using digital imaging for online analysis of constituents in milk", Proc. of SPIE vol. 9525, 95254A, 2015.*
(Continued)

*Primary Examiner* — Jamie J Atala
*Assistant Examiner* — Ayman A Abaza
(74) *Attorney, Agent, or Firm* — Daly Crowley Mofford & Durkee LLP

(57) ABSTRACT

A system for analyzing fluid includes a housing having first and second opposing surfaces spaced to form a fluid chamber, a light source disposed to direct light at the first surface of the housing; and a digital imaging circuit disposed to detect light at the second surface of the housing. The digital imaging circuit includes a pixel array configured to capture one or more digital images of an illuminated fluid. The system also includes a processor configured to: capture multiple digital images of the fluid at different camera exposure levels, calculate a net radiant energy value at a plurality of different integration times within at least two images, calculate a slope of the net radiant energy value with respect to integration time in a selected image, and deter-
(Continued)

mine size distribution and volume fraction of particles within the fluid based on the calculated slope.

26 Claims, 13 Drawing Sheets

(51) Int. Cl.
| | |
|---|---|
| *G01N 33/06* | (2006.01) |
| *G01N 33/14* | (2006.01) |
| *H04N 5/213* | (2006.01) |
| *H04N 5/217* | (2011.01) |
| *H04N 5/225* | (2006.01) |
| *H04N 5/235* | (2006.01) |
| *H04N 7/18* | (2006.01) |
| *G01N 21/51* | (2006.01) |
| *G01N 21/59* | (2006.01) |
| *G01N 21/00* | (2006.01) |
| *G01N 15/00* | (2006.01) |

(52) U.S. Cl.
CPC .............. *G01N 21/59* (2013.01); *G01N 33/06* (2013.01); *G01N 33/14* (2013.01); *H04N 5/213* (2013.01); *H04N 5/217* (2013.01); *H04N 5/2252* (2013.01); *H04N 5/2256* (2013.01); *H04N 5/2354* (2013.01); *H04N 7/183* (2013.01); *G01N 21/00* (2013.01); *G01N 2015/03* (2013.01); *G01N 2015/0693* (2013.01); *G01N 2021/513* (2013.01); *G01N 2021/5957* (2013.01)

(58) Field of Classification Search
CPC ........... G01N 2015/0693; H04N 5/213; H04N 5/217; H04N 5/2252; H04N 5/2256; H04N 5/2354; H04N 7/183
USPC .......................................................... 348/135
See application file for complete search history.

(56) References Cited

U.S. PATENT DOCUMENTS

| | | | |
|---|---|---|---|
| 6,091,492 A * | 7/2000 | Strickland | .......... G01N 15/0211 356/336 |
| 6,122,042 A | 9/2000 | Wunderman et al. | |
| 6,315,955 B1 | 11/2001 | Klein | |
| 6,316,772 B1 | 11/2001 | Egelberg | |
| 6,407,813 B1 | 6/2002 | Lovette et al. | |
| 7,236,237 B2 | 6/2007 | Schmilovitch et al. | |
| 7,450,235 B1 | 11/2008 | Said et al. | |
| 7,943,384 B2 | 5/2011 | Durack et al. | |
| 8,622,128 B2 | 1/2014 | Hegeman | |
| 2005/0202395 A1* | 9/2005 | Edrich | .................. A61L 2/0005 435/2 |
| 2007/0010974 A1 | 1/2007 | Nicoli et al. | |
| 2017/0292874 A1* | 10/2017 | Ramer | ...................... G01J 1/08 |

OTHER PUBLICATIONS

PCT International Preliminary Report dated Oct. 26, 2017 for International Application No. PCT/US2016/027070; 7 pages.
Search Report and Written Opinion of the ISA dated Jul. 15, 2016; for PCT App. No. PCT/US2016/027070; 20 pages.

* cited by examiner

FLUID ANALYSIS USING DIGITAL IMAGERY

RELATED APPLICATIONS

This application is a National Stage filing under 35 U.S.C. 371 of PCT Application No. PCT/US2016/027070, which was filed in the English language on Apr. 12, 2016. This application claims priority to and the benefit of U.S. Provisional Application No. 62/146,456 (filed Apr. 13, 2015) and U.S. Provisional Application No. 62/197,126 (filed Jul. 27, 2015). The applications listed in this section are incorporated here by reference in their entirety.

FIELD

This disclosure relates to analysis of fluids and, more particularly, to analysis of particles in turbid fluids and emulsions such as milk.

BACKGROUND

Scattering, absorption and extinction of electromagnetic radiation passing through an interacting medium can be used to analyze material properties of the medium. The medium may force the electromagnetic radiation to deviate from its trajectory due to non-uniformities of the medium through which the radiation passes. As an example, a photodetector (e.g. a phototransistor or photodiode) can measure the light passing through a material. The pattern and intensity of the measured light provides information about the material and its properties.

Milk is a complex biological fluid with several constituents dispersed or dissolved in an aqueous medium. The composition varies between milk from animals of different species, between milk from animals of the same species, and between milk from the same animal depending on the season, feed and lactation stage. Milk may also include other minor constitutes like somatic cells, urea (non-protein nitrogen), microorganisms and residual compounds, including antibiotics, pesticides and heavy metals.

Fat in milk is present in the form of dispersed spherical globules. Depending on several intrinsic and extrinsic factors, it may or may not be in a crystalline or a semi-crystalline form. A layer of Milk Fat Globule Membrane (MFGM) emulsifies the globules in raw milk. It is a complex biological layer mainly composed of proteins and phospholipids. The diameter of the globules in raw milk varies with species and seasons. Its diameter is usually between 3-5 $\mu$m and up to 10 $\mu$m, and usually follows a lognormal distribution. In processed milk, the size is decreased to 0.7-2 $\mu$m by homogenization to increase globule surface area and promote emulsion stability.

Protein in milk is present as dispersed casein micelles and dissolved whey or serum. The former constitutes approximately 80% of the total milk protein. Casein micelles are stable spherical particles with mean diameter between 100-150 nm, and range between 50-500 nm. Milk is hence a polydisperse emulsion with dispersed particles (fat globules and casein micelles) having widely different particle size distributions. In homogenized milk, both casein and whey proteins are adsorbed to smaller fat globules as emulsifiers and form a layer usually thicker than the original MFGM layer.

The presence of multiple chemical constituents, in different physical forms, and varying concentrations significantly complicates interaction of electromagnetic radiation with milk. Most fundamental signatures due to atomic or molecular absorption from lipids, proteins and lactose lie in the mid-infrared region (2500-25000 nm) of the electromagnetic spectrum. Near-infrared region (780-2500 nm) also exhibits absorption signatures from milk constituents, however with overtones and band overlapping. Laboratory instruments for constituent analysis of milk typically use mid-infrared and near-infrared spectrums. Electromagnetic radiation is also scattered by milk due to the presence of particles of different sizes.

In the UV/Vis region (300-1100 nm), instead of specific bands and peaks of absorbance, a continuum is observed. Interaction is dominated by the scattering of light from fat globules and casein micelles that is strongly dependent on the ratio of particle diameter and incident wavelength. Equipment such as turbidimeters used for estimation of fat concentration measure the extinction of incident light due to scattering by fat globules.

SUMMARY

In an embodiment, a system for analyzing fluid includes a housing having first and second opposing surfaces spaced to form a fluid chamber, a light source disposed to direct light at the first surface of the housing; and a digital imaging circuit disposed to detect light at the second surface of the housing. The digital imaging circuit includes a pixel array configured to capture one or more digital images of an illuminated fluid. The system also includes a processor configured to: capture multiple digital images of the fluid at different camera exposure levels, calculate a intensity value at a plurality of different integration times within at least two images, calculate a slope of the net radiant energy value with respect to integration time in a selected image, and determine a size distribution and volume fraction of particles within the fluid based on the calculated slope. One or more of the following features may be included. The processor may be configured to determine a property of a fluid based on the predetermined particle size. The fluid may be milk and the property may be a fat and/or protein content.

The opposing surfaces of the housing may be clear. At least one of the opposing surfaces may include a light filter. The light source may include one or more of: a laser diode, an LED, an incandescent lamp, and/or a mercury/halogen lamp. The system may include a lens positioned to focus an image of fluid on the pixel array.

The processor may be further configured to filter noise from the digital images. The processor may be configured to filter the noise by averaging pixel readings at each radial distance from a center of the digital images. Calculating the net radiant energy value may include performing a sum or integration of pixel readings of the digital images.

The processor may be further configured to calculate a logarithmic parameter of the digital images; to calculate the logarithmic parameter by calculating a standard deviation of pixel readings in each digital image and performing a best logarithmic fit of the standard deviation values with respect to integration time; and/or to control the light source.

The light source may include multiple light sources and the processor may be configured to capture the digital images illuminated by one or more of the multiple light sources.

The processor may be further configured to perform regression analysis using one or more regression models and the calculated slope to compute particle size distribution and volume fraction of the fluid sample; and/or to compute a logarithmic parameter for use in the one or more regression models.

In another embodiment, a method for analyzing a fluid includes: illuminating a fluid sample with a light source; capturing, with a digital camera circuit, a plurality of digital images of the illuminated fluid sample at different camera exposures; calculating, with a processing circuit, a net radiant energy value at a plurality of different integration times within at least two images; calculating, with the processing circuit, a slope of the net radiant energy value with respect to integration time in a selected image; and determining a size distribution and volume fraction of particles within the fluid sample based on the calculated slope.

One or more of the following features may be included. A property of a fluid may be determined based on the predetermined particle size. The fluid may be milk and the property may be a fat and/or protein content.

The fluid sample may be pumped into a housing having a chamber between two opposing, clear surfaces. At least one of the surfaces may include a light filter. The light source may include a Laser Diode. A lens may be positioned to focus an image of fluid on the pixel array. Noise may be filtered from the digital images. Filtering the noise may include averaging pixel readings at each radial distance from a center of the digital images. Calculating the net radiant energy value may include performing a sum or integration of pixel readings of the digital images.

BRIEF DESCRIPTION OF THE DRAWINGS

The foregoing features may be more fully understood from the following description of the drawings. The drawings aid in explaining and understanding the disclosed technology. Since it is often impractical or impossible to illustrate and describe every possible embodiment, the provided figures depict one or more exemplary embodiments. Accordingly, the figures are not intended to limit the scope of the invention. Like numbers in the figures denote like elements.

DETAILED DESCRIPTION

Figure 1:
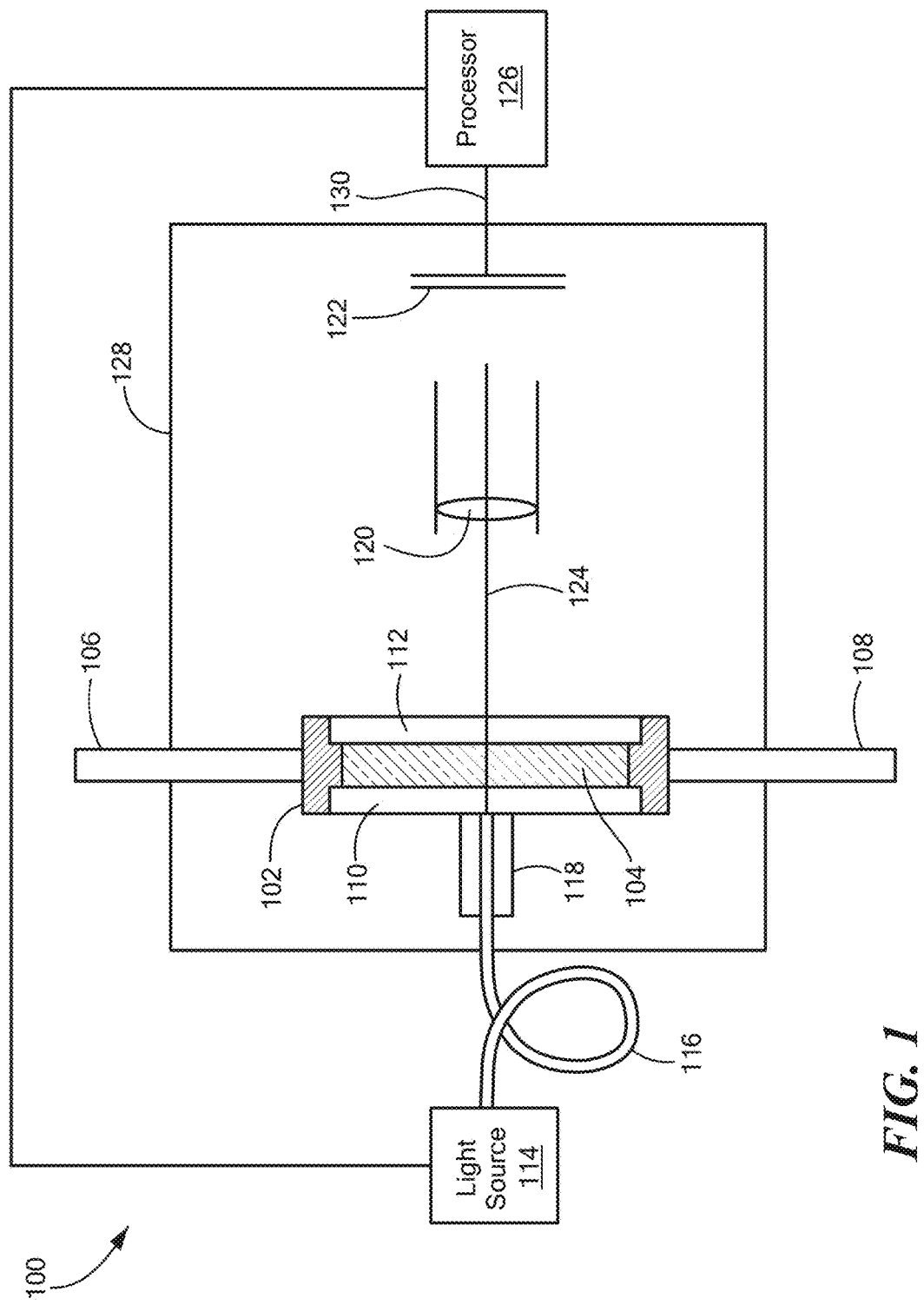
FIG. 1 is a block diagram of an apparatus for analyzing a fluid.

FIG. 1 is a schematic diagram of an apparatus 100 for analyzing a fluid. The fluid may be any emulsion or suspension having dispersed particles, or any fluid that may scatter or absorb radiation incident to fluid.

Apparatus 100 includes a housing 102 having a chamber 104 or cavity within, capable of containing a sample of the fluid to be analyzed. The housing may include an intake tube 106 and outlet tube 108 through which fluids may be received into the housing and expelled from the housing. The fluid under analysis may be pumped through intake tube 106 into chamber 104 for analysis. When the analysis is complete, the sample may be pumped or sucked out of chamber 104 through outlet tube 108. In another embodiment, apparatus 100 may include one tube that can be used for both introducing the sample fluid into chamber 104 and extracting the sample fluid from chamber 104 when analysis is complete. Apparatus 100 may also include multiple intake and/or multiple outlets for the fluid.

Housing 102 may also include panels 110 and 112 on opposite sides of housing 102. Panels 110 and 112 may be transparent or translucent to allow light to pass through panels 110 and 112 to the fluid sample under analysis within chamber 104. In an embodiment, panels 110 and 112 may be made of glass, quartz, plastic, or any other type of optically clear material.

Panels 110 and 112 may be shaped so that they do not focus or disperse light incident thereon as would a convex or concave lens. In other words, panels 110 and 112 may be flat e.g., plane-plane surface or lens, like windows, so that the direction of light passing through the panels is not substantially altered. In another embodiment, one or both panels 110 and 112 may be provided as lenses shaped to concentrate, disperse, or otherwise change the direction of light (or other radiation) incident on surfaces thereof.

In embodiments, panel 110 and/or 112 may include light filters such as polarizing filters, monochromatic filters, neutral-density absorptive filters, color filters, etc. The filters may be placed on the outside of, inside of, or integrated into the panels. In other embodiments, the filters may be separate from the panels and placed within the light path between light source 114 and digital camera circuit 122.

Apparatus 100 may also include a light source 114, which may be an optoelectronic source of radiation, such as a light emitting diode. Light source 114 may also be a collimated laser light, or any other type of light source including, but not limited to, a collimated or diffuse light source, a coherent or an incoherent light source, a monochromatic or polychromatic light source, a polarized or unpolarized light source, etc. Examples include, but are not limited to: LEDs which may be diffuse and monochromatic or polychromatic light sources; laser diodes which may be collimated, coherent and monochromatic light sources; incandescent lamps which may be diffuse polychromatic light sources; or halogen/mercury lamps which may be diffuse and monochromatic or dichromatic light sources. In embodiments, diffuse light sources may be coupled with a collimator lens or filter system to produce a collimated light output. Polychromatic light sources may be coupled with monochromatic filters to produce a particular wavelength or wavelength band. Unpolarized light sources may be coupled with a polarizing lens or filter to produce polarized light.

In embodiments, light source 114 may include multiple light sources chosen from the types described above. Light source 114 may include multiple sources of the same type, or multiple sources of different types. Light source 114 may have multiple light sources that may have different nature and types. The nature, type, wavelength may be selected or tuned by the controller. In some embodiments, light source 114 may be replaced (or supplemented) by a radiation source (not shown) that produces radiation outside the visible spectrum. In embodiments, the light source may produce radiation near infrared and/or ultraviolet bands, e.g. radiation with wavelength ranging from about 800 nm to 2500 nm.

An optical cable 116 may be coupled between light source 114 and panel 110 to direct the light produced by light source 114 toward the surface of panel 110. Light incident on the panel 110 illuminates fluid within chamber 104. Coupling 118 may be positioned adjacent or attached to panel 110 to securely hold optical cable 116 proximate panel 110. In an embodiment, coupling 118 may be provided as an SMA connector.

Coupling 118 may be centered on panel 110 or, alternatively, may be positioned at any location on panel 110 such that emissions from source 114 illuminate fluid within chamber 104. In addition, optical cable 116 may be any mechanism, such as an optical fiber, a light pipe, etc. capable of directing light from light source 114 onto the fluid in chamber 104. In some embodiments, energy emitted from source 114 propagates through free space and impinges upon a surface of panel 110.

Apparatus 100 also includes an optical lens 120 and a digital imaging circuit (e.g., a digital camera) 122. Lens 120 may be positioned and shaped to focus an image of panel 112 and the fluid within chamber 104 onto the digital imaging circuit 122. Lens 120 may be a wide angle lens, a telephoto lens, or any type of optical lens that can focus an image of the fluid to be captured by the digital imaging circuit 122. In an embodiment, lens 120 may include an aperture and/or shutter that can open and close to expose the image to digital imaging circuit 122. As shown in FIG. 1, digital imaging circuit 122 and light source 114 may be positioned on opposite sides of housing 102.

Digital imaging circuit 122 may have an imaging circuit, which may include two-dimensional array of CCD and/or CMOS sensors to capture images of the fluid. Digital camera circuit 122 may be the same as or similar to digital camera circuits and chips found in commercially available digital cameras, smart phones, etc.

In an embodiment, coupling 118, lens 120, and digital imaging circuit 122 may be aligned on the same axis 124 so that the light produced by light source 114 is in the center of the digital images produced by digital camera circuit 122. In other embodiments, these elements may not be aligned on the same axis, and the light produced by light source 114 may not be centered in the digital images produced by digital camera circuit 122.

Fluid analysis apparatus 100 may also include a processor 126 to process the captured digital images from digital imaging circuit 122 and an enclosure 128 surrounding some or all of the elements of apparatus 100. In an embodiment, enclosure 128 is a light-tight enclosure that reduces, and ideally entirely prevents, ambient light from entering and interfering with the capturing of digital images. The interior of enclosure 128 may be colored black to absorb any stray light within the enclosure. Other light absorption techniques may also be used. Enclosure 128 may also have one or more openings to allow intake tube 106, outlet tube 108, and any electrical wires or cables (such as electrical cable 130 coupled between digital camera circuit 122 and processor 126) to pass through the enclosure.

A control line 132 can be coupled between processor 126 and light source 114 to allow processor 126 to control light source 114. Processor 126 may send control signals over control line 132 to turn light source on and off. If light source 114 contains multiple types of light sources as described above, processor 126 can turn the individual types of light sources on and off as desired. For example, if light source 114 includes LED lights, laser diode lights, and an incandescent light, processor 126 may activate any one or any combination of the lights. If light source 114 contains variable or tunable light sources, processor 126 can modify the output of individual light sources as desired. For example, processor 126 may vary the wavelength, power and polarization of individual light sources. In an embodiment, processor 126 may capture multiple digital images of light through the sample fluid using a different light source, or a different combination of light sources, for each image.

In operation, a sample fluid, such as unprocessed milk, is pumped, moved or otherwise provided into chamber 106. For example, the fluid may be pumped through intake pipe 106 into chamber 104. Light source 114 illuminates the sample fluid, and particles or other elements within the fluid may scatter at least some of the light. Digital camera circuit 122 may then capture one or more images of the sample fluid and provide them to processor 126. Processor 126 may process the images and provide an analysis of the sample fluid in a manner to be described below in conjunction with FIGS. 2-12.

Figure 1A:
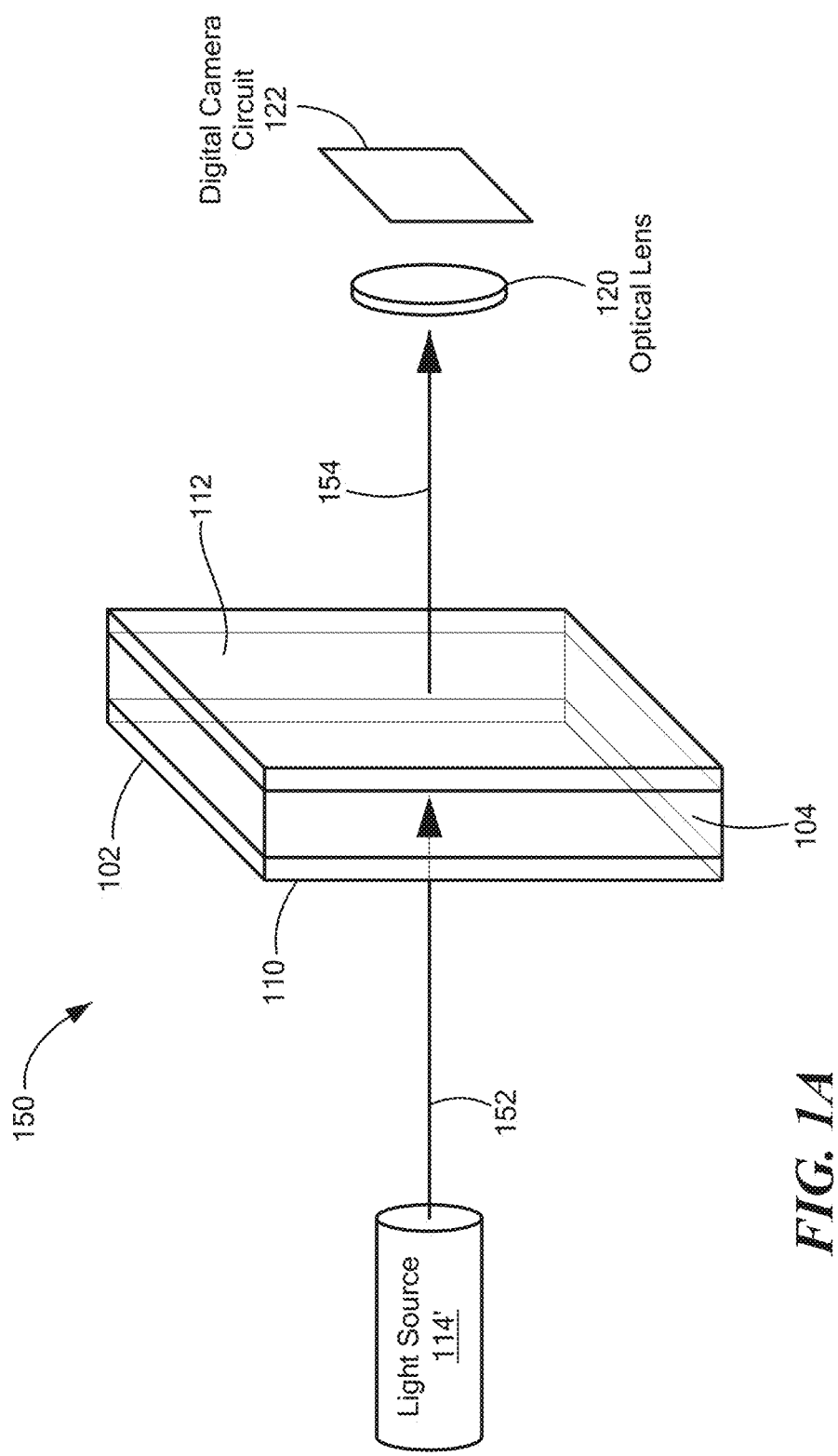
FIG. 1A is an isometric diagram of an apparatus for analyzing a fluid.

FIG. 1A is an isometric view of an apparatus 150 for analyzing a fluid, which may be the same as or similar to apparatus 100. Apparatus 150 includes a housing 102, panels 110 and 112, chamber 104, lens 120, and digital camera circuit 122 as described above. Apparatus 150 may also include a light source 114', positioned to direct light radiation onto panel 110. As shown, light source 114' may be in a spaced relation to (i.e. separate from) panel 110 and may direct light radiation 152 through free space onto panel 110. Radiation 154 exiting panel 112 may be focused by lens 120 and captured as a digital image by digital camera circuit 122.

Figure 2:
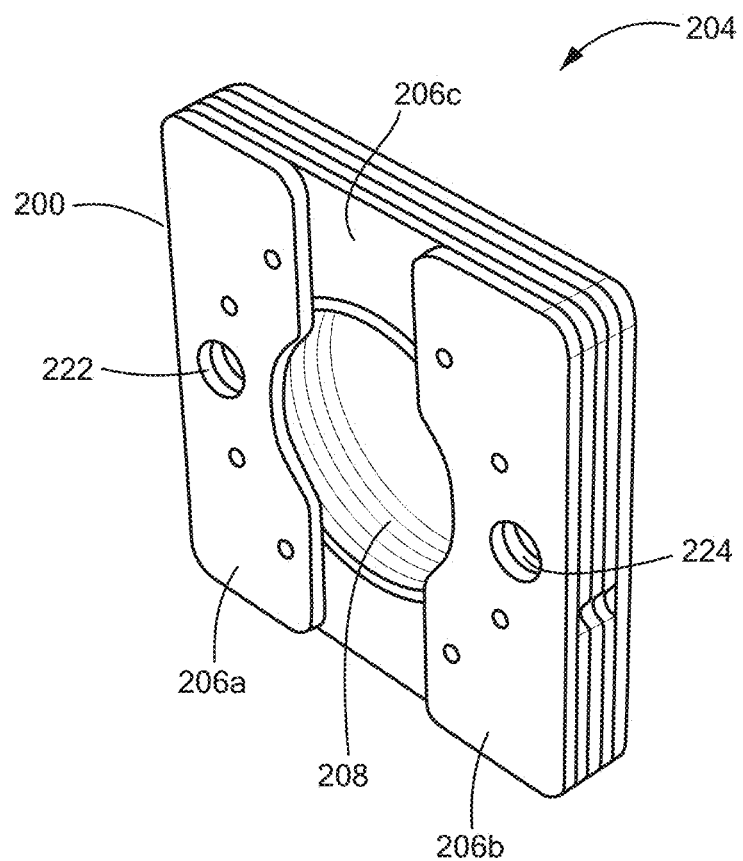
FIG. 2 is an isometric view of a housing for analyzing a fluid.
Figure 2A:
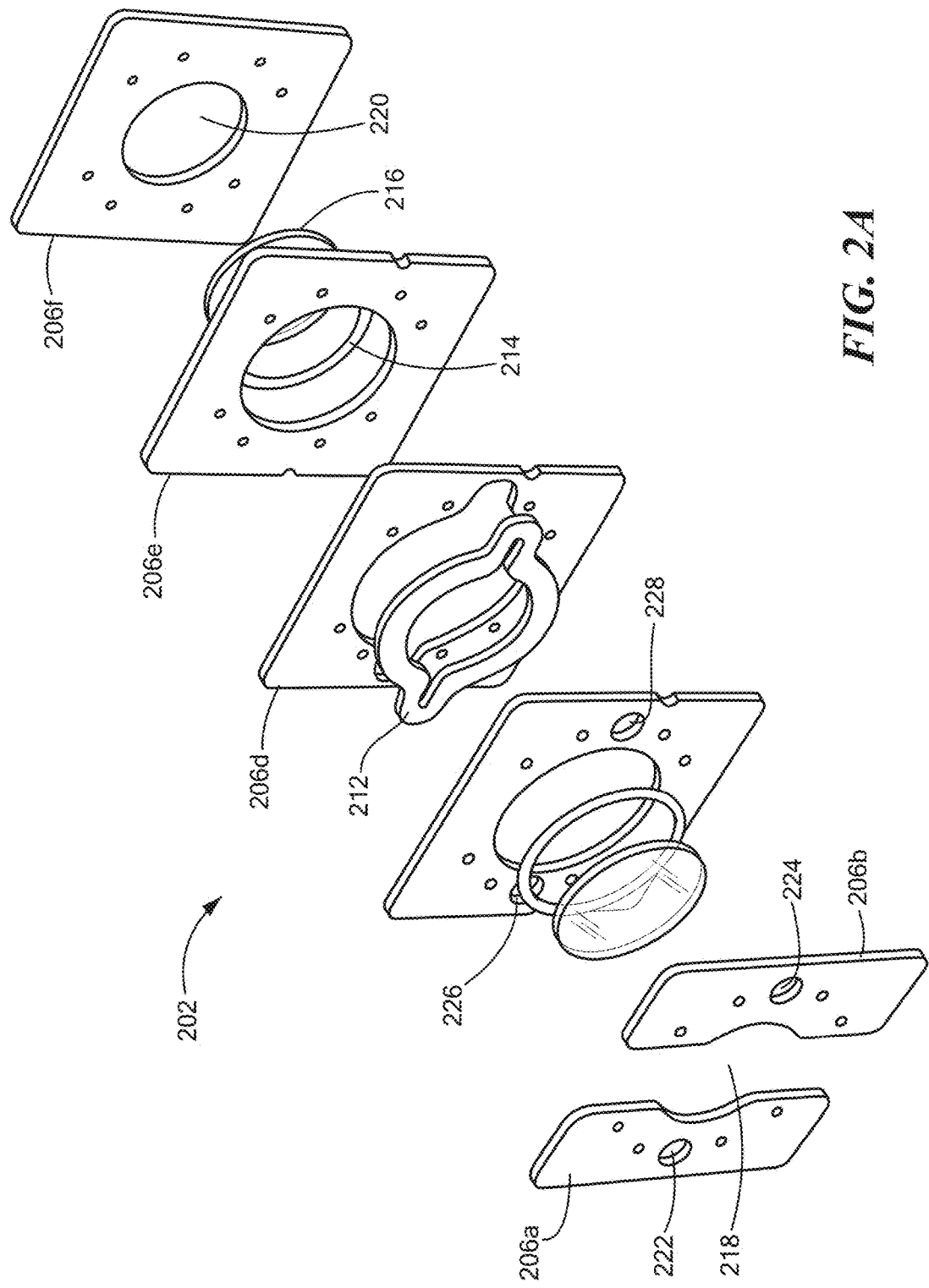
FIG. 2A is an exploded view of the housing of FIG. 2 for analyzing a fluid.

Turning to FIGS. 2 and 2A in which like elements are provided having like reference designations, a housing 200 which may be the same as or similar to housing 102 in FIG. 1, comprises a series of plates 206a-206f. Panel 208 (which may be the same as or similar to panel 110 and/or panel 112 in FIG. 1) and O-Ring 210 are held in place between plate 206c and plates 206a and 206b. In another embodiment, O-Ring 210 is sandwiched between panel 208 and the circular hole in 206c. Plates 206a and 206b constrain the panel 208 and O-Ring 210 such that they do not move out of their location.

A gasket 212 is sandwiched between plates 206c and 206d. Another O-Ring 214 and a second panel 216 (which may be the same as or similar to panel 110 and/or panel 112) lie between plates 206e and 206f. In another embodiment, gasket 212 is sandwiched between plates 206c and 206e. It lies flat in the cavity in plate 206d. The cavity in 206d may be bigger than the gasket, such that the compressed gasket expands and fills the gap When assembled, O-Rings 210 and 214 and gasket 212 space panel 208 and panel 216 apart, forming a chamber between them into which a fluid sample can be introduced. In an embodiment, the gap between the inside surfaces of panels 208 and 216, forming the chamber, may be 1 mm. In other embodiments, the gap may vary from about 0.1 to about 10 mm. The size of the gap may be chosen based on a desired quality of results, which may vary with sample thickness. The best gap is usually chosen based on lab experiments at different gaps during the design phase. In embodiments, fluids with larger particles, or those with fewer particles may return higher quality results if sampled in a larger gap.

The size of the gap may also be chosen based on adhesion of the sample fluid to the surfaces of panels 208 and 206. A relatively narrow gap may restrict fluid flow, and therefore allow the fluid adhere to internal surfaces.

The diameter of the panel may also be chosen based on quality of results. In an embodiment, the diameter of the panel is large enough to observe the entire spread of diffused light through the sample fluid. In one embodiment, the diameter of panels 208 and 216 is 25 mm. In other embodiments, the diameter of panels 208 and 216 may vary between about 5 mm to about 50 mm. The diameter of panels 208 and 216 may be, but is not required to be the same diameter.

Outer plates 206a, 206b, and 206f form openings 218 and 220. In an embodiment, a light source (such as light source 114 may illuminate the fluid by radiating light through opening 218. A digital camera circuit and lens (such as digital camera circuit 122 and lens 120) may be positioned adjacent to opening 220, opposite the light source, to record an image of the illuminated fluid.

Plates 206a, 206b, and 206c may also include openings 222, 224, 226, and 228 which, when housing 200 is assembled, may act as inlet and outlet conduits through which the sample fluid can be introduced and removed from the chamber between panels 208 and 216. Housing 200 may be assembled with adhesives or any type of fasteners. In an embodiment, housing 200 may be assembled with removable screws so that it can be taken apart and repaired and/or cleaned. In embodiments, the plates may be made from stainless steel or other corrosion resistant materials, and may have polished surfaces to prevent deposits. The plates may be welded together and may be formed by machining one or more pieces pf suitable metal or other material.

Figure 3:
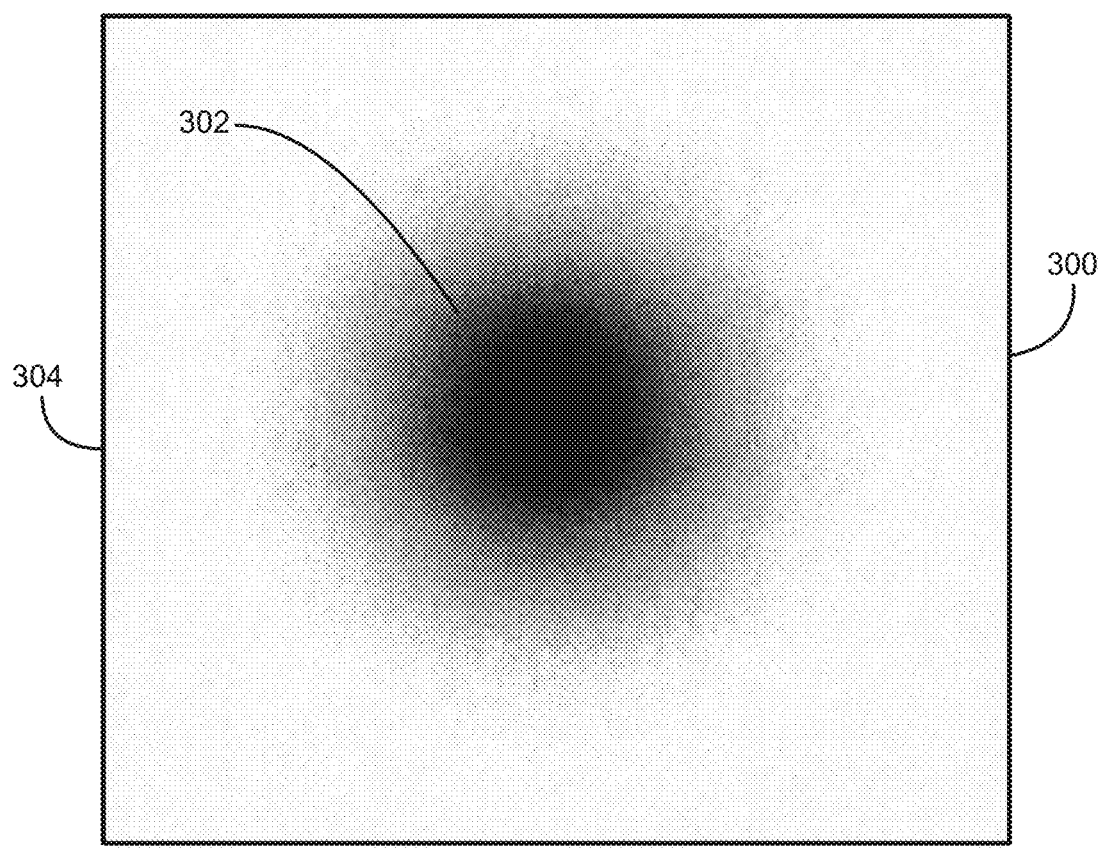
FIG. 3 is a captured digital image of light through a fluid.

FIG. 3 is a digital image 300 of light through a sample fluid that may be captured by digital imaging circuit 122. A processor (e.g., processor 126 described above in conjunction with FIG. 1) may capture and process images like digital image 300 in order to analyze the fluid. Digital image 300 shows a spatial radiant energy transmission pattern having a high radiant energy in the center position 302 and less radiant energy at the edges 304. As noted above, a light source (e.g., light source 114 in FIG. 1) may be centered on a panel (e.g., panel 110 in FIG. 1) so as to and provide the highest intensity illumination in the center of the fluid sample. Thus, in digital image 300, the point of highest radiant energy is in center position 302. Because digital image 300 is a negative image, the darker areas correspond to areas of greater radiant energy. In image 300, the light source and digital image are both centered. However, the center position 302 need not be coincident with image center or light source, and in some cases the light source and camera may not be positioned on the same axis.

Figure 4:
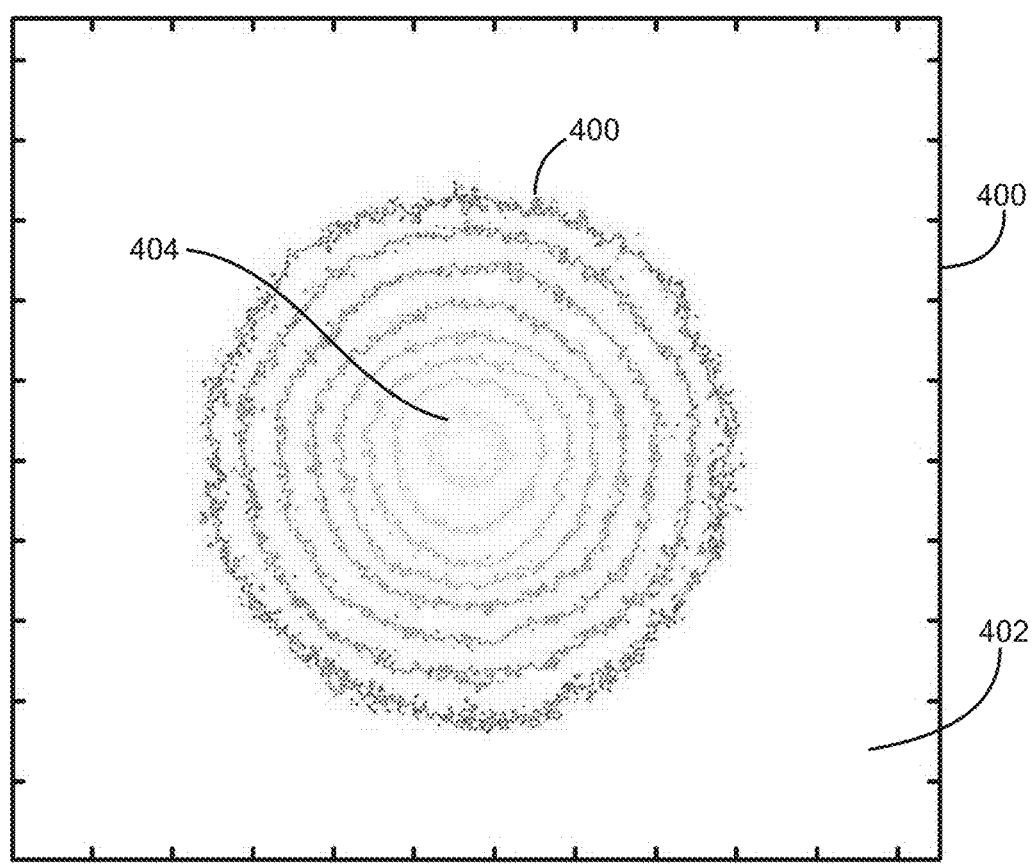
FIG. 4 is a topographical plot of radiant energy of light through a fluid.

FIG. 4 shows a topographic graph 400 of digital image 300 (FIG. 3). The horizontal and vertical axes represent the X and Y dimensions (e.g. pixel locations) of image 300. Each ring 400 corresponds to an area of particular radiant energy or pixel reading, with the outer area 402 representing the lowest pixel reading and the inner ring 404 representing the greatest pixel reading of the image.

Figure 5:
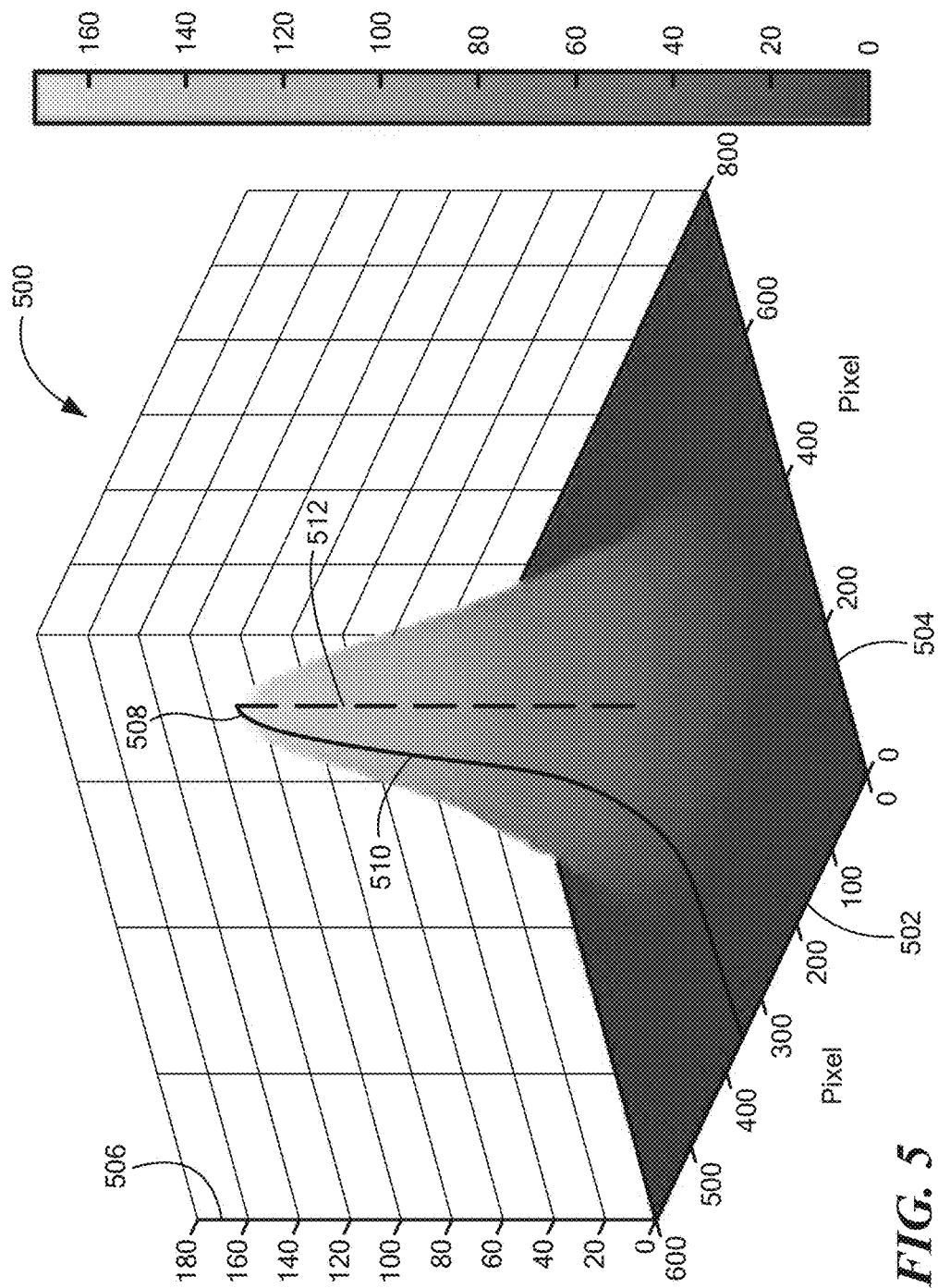
FIG. 5 is three-dimensional plot of radiant energy of light through of a fluid.

FIG. 5 shows a three-dimensional plot 500 of digital image 300 (FIG. 3). Axis 502 and axis 504 represent the X and Y dimensions (e.g. the pixels) of digital image 300. Axis 506 represents the reading at each pixel, i.e. the radiant energy picked up by each pixel (measured as the digital pixel reading) at a particular X and Y location. As noted above, the image was captured with a light source centered in the sample. Thus, the point of highest radiant energy can be found at point 508, the peak of the three-dimensional curve in the center of the X and Y plane. The three dimensional curve is the same as or similar to a 2-Dimensional Gaussian or normal curve due to scattering and diffusion of incident radiation by the fluid sample. The radiant energy is greatest at the point of the light source at location 508, but the energy diminishes as it moves and is scattered away from that point toward the edges of the image.

Digital images are subject to noise from various sources, thus the images may be processed—(e.g., via processor 126 in FIG. 1) to provide image correction and compensation to increase accuracy of processing and analysis of the image. Noise in a digital image can come from various sources. For example, a digital imaging circuit may introduce noise due to non-linearity in the conversion of detected photons or radiant energy into an electrical signal. The analog output of the detector for each pixel may be related to the exposure of the image by a power law relation. Another example source of noise is referred to as photon response non-uniformity, which creates a fixed pattern noise in the image proportional to the exposure level or integration time.

Dark current in each pixel can also create a noise floor (which can be understood as thermal noise). Photon shot noise can be introduced in the image due to the quantum nature of photons. In addition, digital image sensors have finite dynamic range. The lower limit of the dynamic range is governed by the noise floor, and the upper limit is governed by the well capacity of the sensor. Exposure beyond the upper limit results in noise due to saturation of a detected pixel.

Figure 6:
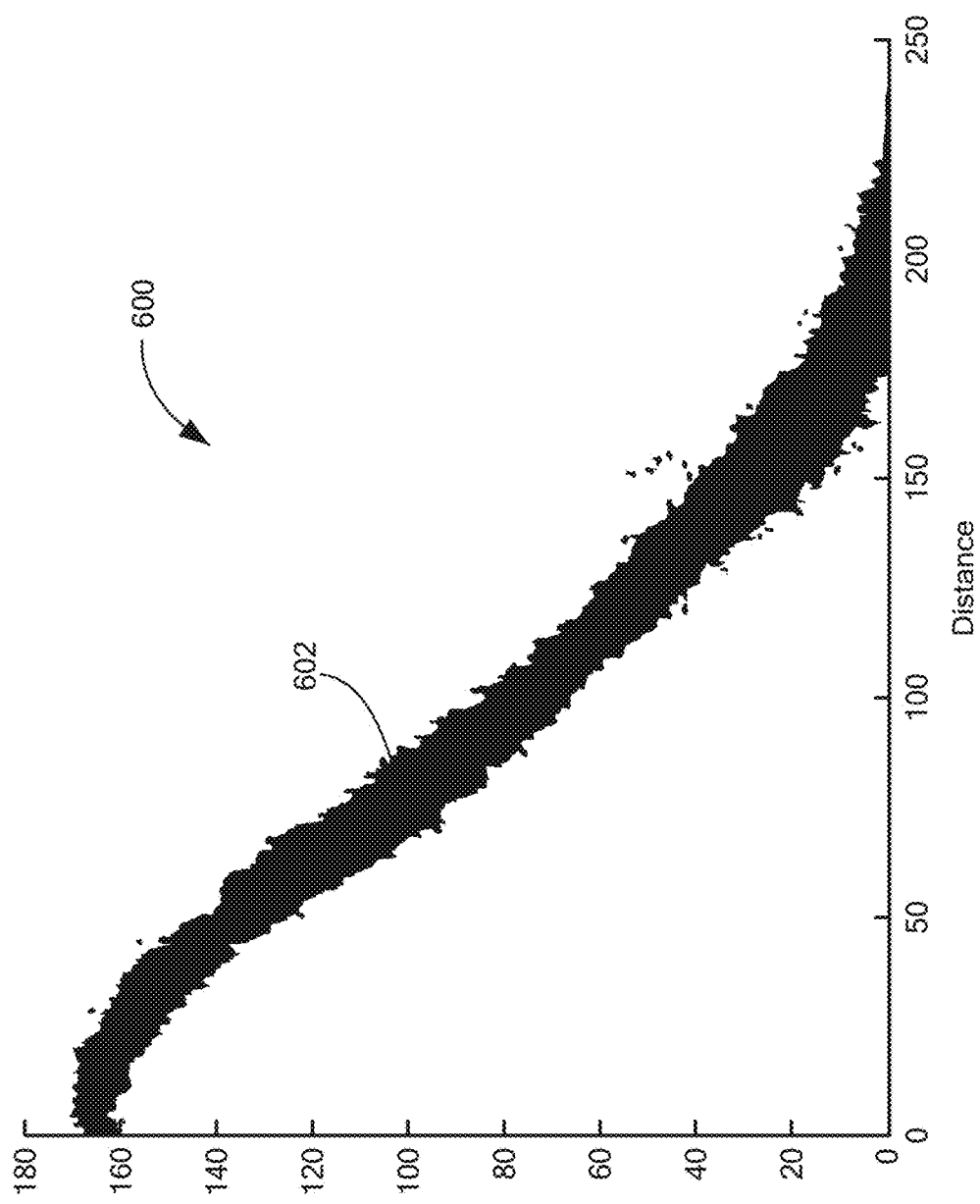
FIG. 6 and FIG. 7 are plots of radiant energy vs. radial distance from a center.

A processor, such as processor 126 in FIG. 1, may be configured to compensate for and reduce the effect of noise during processing of the image. As seen in FIG. 5, the radiant energy has a radial distribution. The plot in FIG. 6 is a two-dimensional plot 600 of such a radial distribution. The vertical axis of plot 600 represents radiant energy or pixel reading of the image and the horizontal axis represents the radial distance from the center of the image. Curve 602 may represent a slice of the three-dimensional curve 500 in FIG. 5. For example, curve 602 may correspond to curve 510 or another radial slice of the three-dimensional curve. In another embodiment, curve 602 may be an average or an aggregation of readings from multiple radial slices taken around the three-dimensional plot 500 in FIG. 5. In another embodiment, each pixel in three-dimensional plot 500 is represented in curve 602. For example, for each reading in three-dimensional plot 500, processor 126 may calculate a distance of the pixel from centerline 512. The intensity of the light reading for that pixel may then be plotted against the calculated distance to form curve 602. In an embodiment, the pixel readings are classified into bins according to the radial distance.

Figure 7:
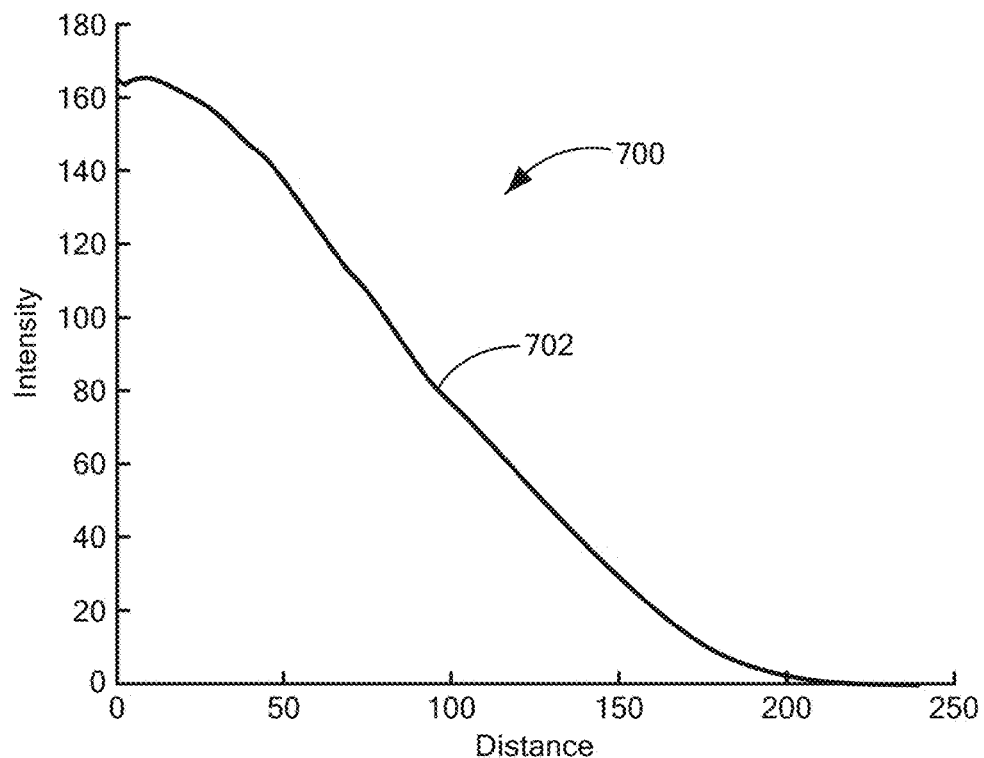

Curve 602 includes noise, a part of which manifests as the thickness of curve 602. The impact of the noise may be reduced by averaging the light intensity readings at each radial distance. Referring also to FIG. 7, curve 702 is the result of averaging the readings in curve 602 to reduce noise.

Noise in the image data may be further reduced through various techniques. For removing the inaccuracies due to the noise floor and dynamic range limits, a processor such as processor 126 in FIG. 1, may capture multiple images for each fluid sample and illumination state. In an embodiment, processor 126 may capture a first image at a relatively low exposure level, and then take subsequent images at increasing exposure levels until saturation of the image is detected. Exposure level can be increased by increasing integration time of the optical sensor and/or by providing a larger aperture of exposure (in the case where lens 120 includes an aperture). Exposure level may also be increased by increasing the power of the incident light provided by light source 114.

The number of images captured may be a predetermined number, or may be determined by increasing the exposure level until saturation of the image is reached. In an embodiment, ten to twenty images of each fluid sample may be captured. However, any number of samples may be used. Increasing the number and size (e.g. megapixels) of the images may increase the accuracy of the result. However, acquiring more images and/or processing larger images may require a longer testing duration. The number and size of images may be chosen based on desired accuracy of result and desired test time.

By capturing images until saturation is reached, the entire dynamic range of digital camera circuit 122 may be utilized for a given fluid sample. Each captured image may be corrected, compensated, and averaged as described above in relation to FIG. 3-FIG. 7, and the radial distribution of intensity may be obtained after averaging.

Figure 8:
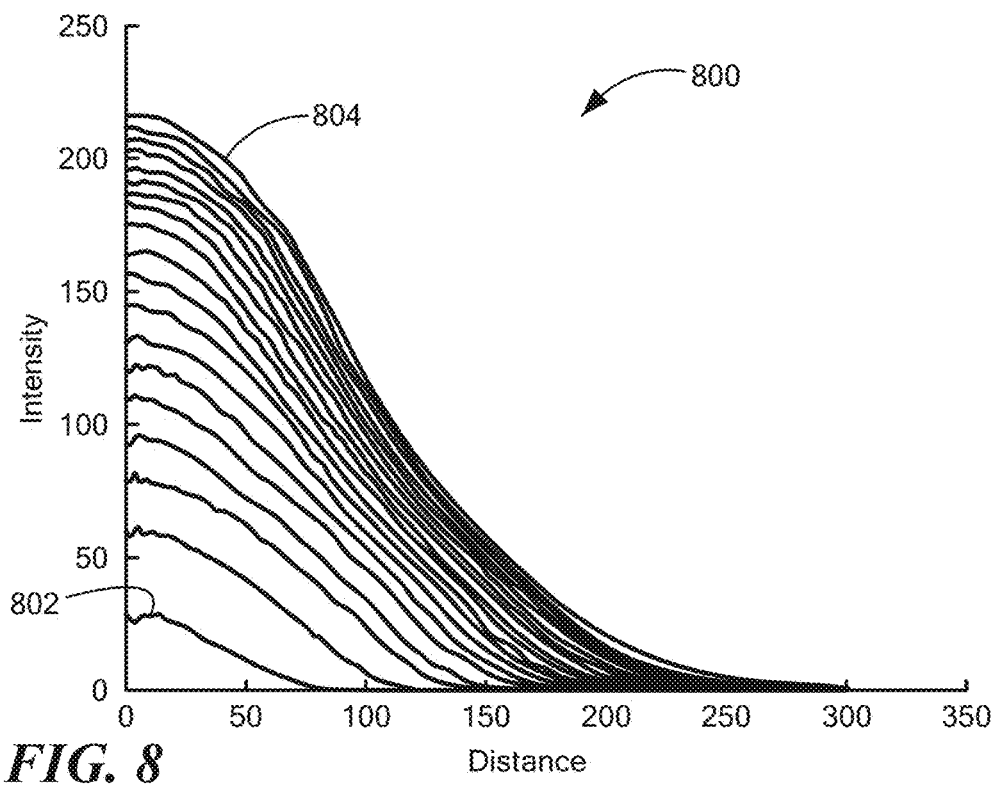
FIG. 8 is a plot of multiple curves representing radiant energy at different integration times vs. radial distance from a center of a fluid.

The result is illustrated in FIG. 8, which includes a plot 800 of radiant energy curves of multiple exposure levels of a single fluid sample. Each curve represents a different exposure level. For example, curve 802 represents the radiant energy of the captured image taken under the lowest exposure level setting and curve 804 represents the radiant energy of the captured image taken under the highest exposure level setting. The middle curves represent images of intermediate exposure level settings.

The curves in FIGS. 5 and 8 may be used to calculate or estimate a value representing the net radiant energy of radiation exiting from the fluid sample. The exiting radiant energy can be represented by performing an integration of each curve over radial distance. The integration may be performed on the pixels in the 3D plot 500 and/or the 2D plots 600, 700, or 800. Alternatively, a summation of the pixel readings represented in each curve will result in a value representing the net radiant energy of light radiation in an image.

Figure 9:
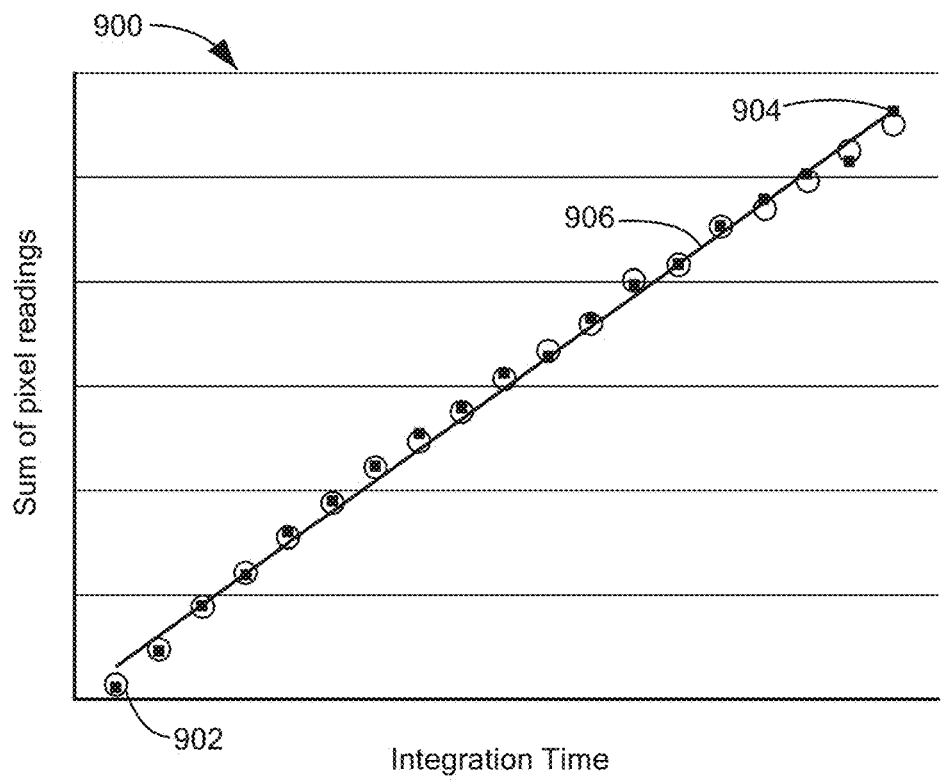
FIG. 9 is a plot of the sum of pixel readings vs. integration times of the multiple curves of FIG. 8.

Referring to FIG. 9, the sum of the pixel readings for each curve in plot 500 is shown as a point in plot 900. For example, point 902 represents the summation of pixel readings of curve 802 and point 904 represents the summation of pixel readings of curve 804. The intermediate points represent the summation of pixel readings of the intermediate curves in plot 500.

As shown, the summations of pixel readings are plotted against integration time.

Processor 126 may calculate a best linear fit of the summations of pixel readings, as illustrated by curve 906. The slope of curve 906 may be used to compute the effective extinction coefficient $\sigma$ of the fluid sample. The negative logarithm of the slope of curve 906 can be linearly related to the effective extinction coefficient $\sigma$ for fluid samples. The extinction coefficient $\sigma$ is defined by the Beer Lambert Law as a linear function of volume fraction and particle size. Effective values of the extinction coefficient $\sigma$ may vary from the value predicted using Beer-Lambert Law due to diffusion and multiple scattering, and may be predicted more accurately by Radiative Transfer Analysis or Monte-Carlo Ray Tracing.

Figure 10:
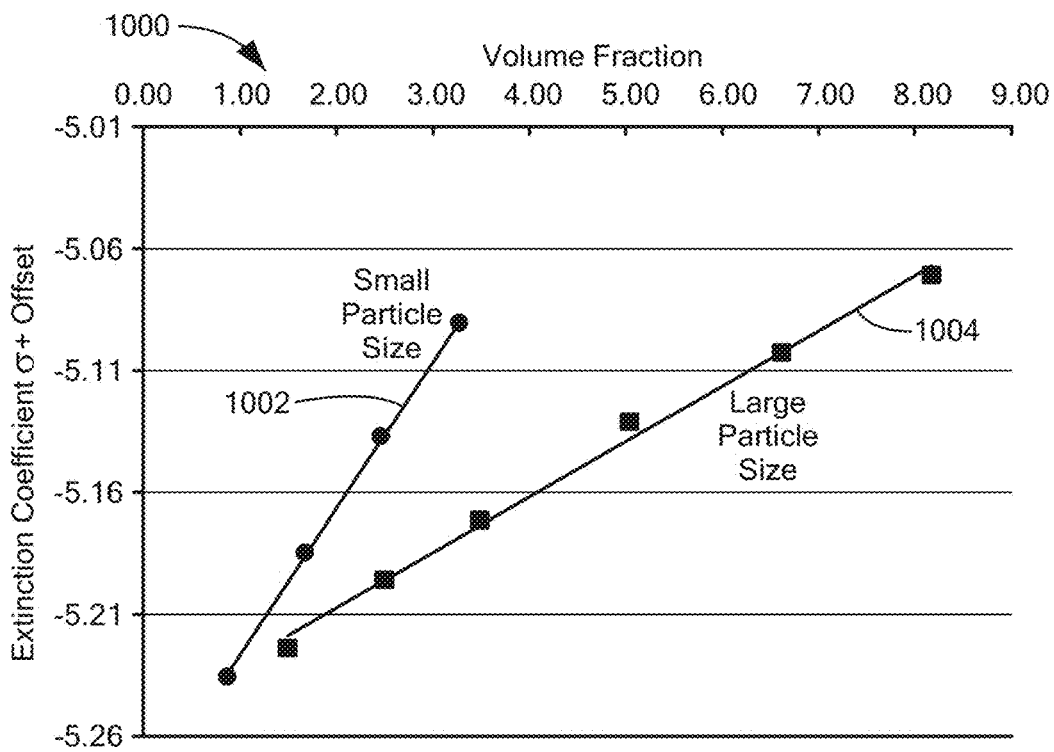
FIG. 10 is a plot of the negative logarithm of the slope of the curve in FIG. 9 for two types of emulsion samples having different particle sizes.

FIG. 10 contains a plot 1000 of the negative logarithm of the slope of curve 906 for two different types of fluid samples, one type with small particle sizes (represented by curve 1002) and the other type with larger particle sizes (represented by curve 1004), with respect to the volume fraction of the particles. As shown in FIG. 10, the small particle size results in curve 1002 having a relatively steep slope and the large particle size results in curve 1004 having a relatively shallow slope. These curves show that the negative logarithm of the slope is linearly dependent on both particle size and volume fraction. If either particle size or volume fraction is known, the other property can be found using the negative logarithm of the slope.

Figure 10A:
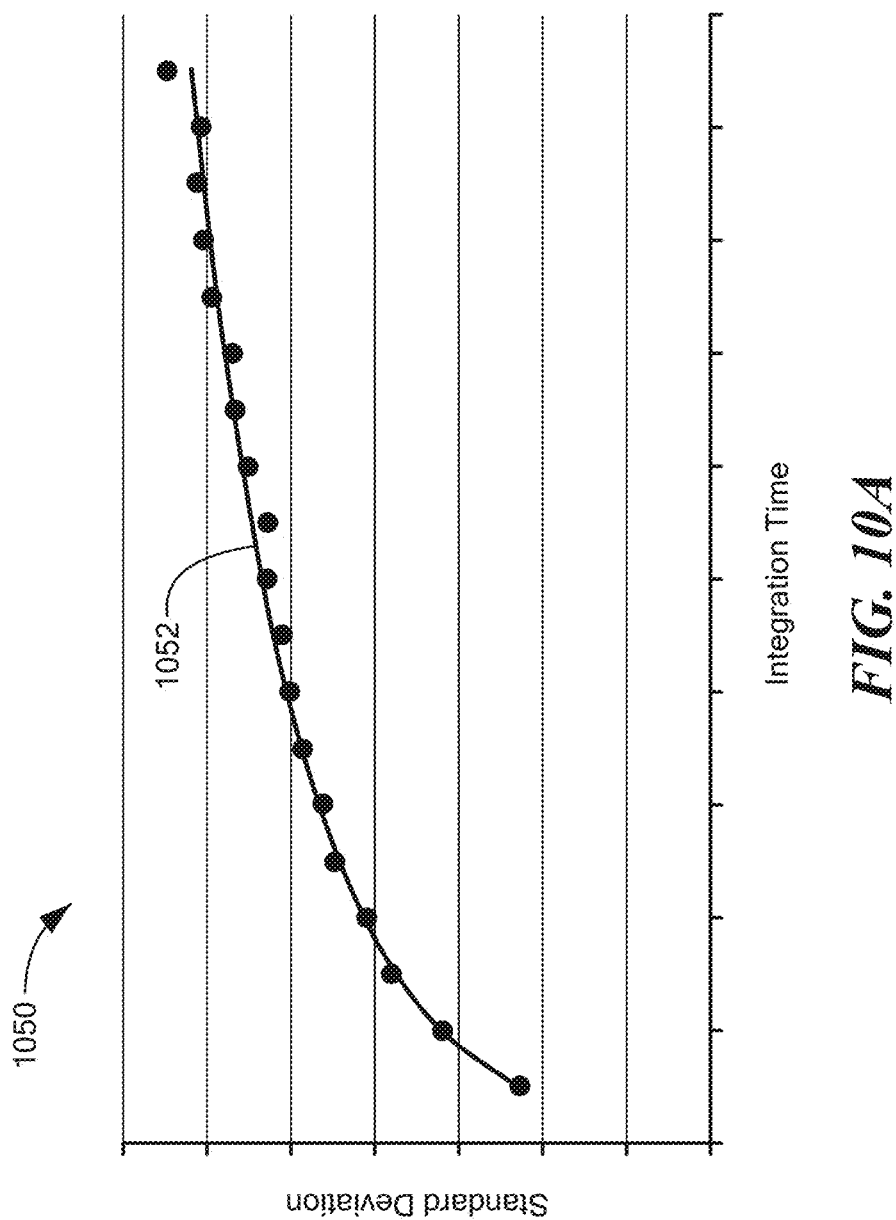
FIG. 10A is a plot of the standard deviation of pixel readings vs. integration times of the multiple curves of FIG. 8.

Referring to FIG. 10A, processor 126 may also use the curves in FIGS. 5 and 8 to calculate or estimate a value representing the spatial distribution of radiation exiting from the fluid sample. The spatial distribution can be represented by calculating the standard deviation of each 2D Gaussian plot (e.g. plot in FIG. 5 for each curve in FIG. 8). Plot 1050 includes a curve 1052 comprising the calculated standard deviation for each curve in FIG. 8 (on the vertical axis) plotted against the integration (i.e. exposure) time of each image (on the horizontal axis).

The points in plot 1050 follow a logarithmic pattern. Thus, processor 126 may calculate a best logarithmic fit to produce curve 1052, represented by the following equation, where y is the standard deviation, x is the integration time, b is an offset, and a is a scalar multiplier:

$$y = a \cdot \ln(x) + b$$

The variable a may be referred to as the "Logarithmic Parameter." Both the sum of the pixel readings (i.e. the net radiant energy in FIG. 9) and the logarithmic parameter may be dependent on particle size and particle volume fraction of the sample fluid. Using the net radiant energy and the logarithmic parameter, standard regression and modeling techniques may be used to extract the particle size and volume fraction from the measured net radiant energy and logarithmic parameter.

When the above analysis is performed on different fluid samples, it may be possible to distinguish the samples based on extinction coefficient (slope) and spatial distribution (logarithmic parameter). The two measured values can be used to identify the particle size distribution and volume fraction of the fluid sample. The above analysis can be repeated at different illumination conditions (wavelength, polarization etc.) for fluid samples with more than one band of particle sizes. If the sample is milk, for example, the detected particle sizes and volume fractions can be used to analyze the protein and/or fat content of the sample.

Figure 11:
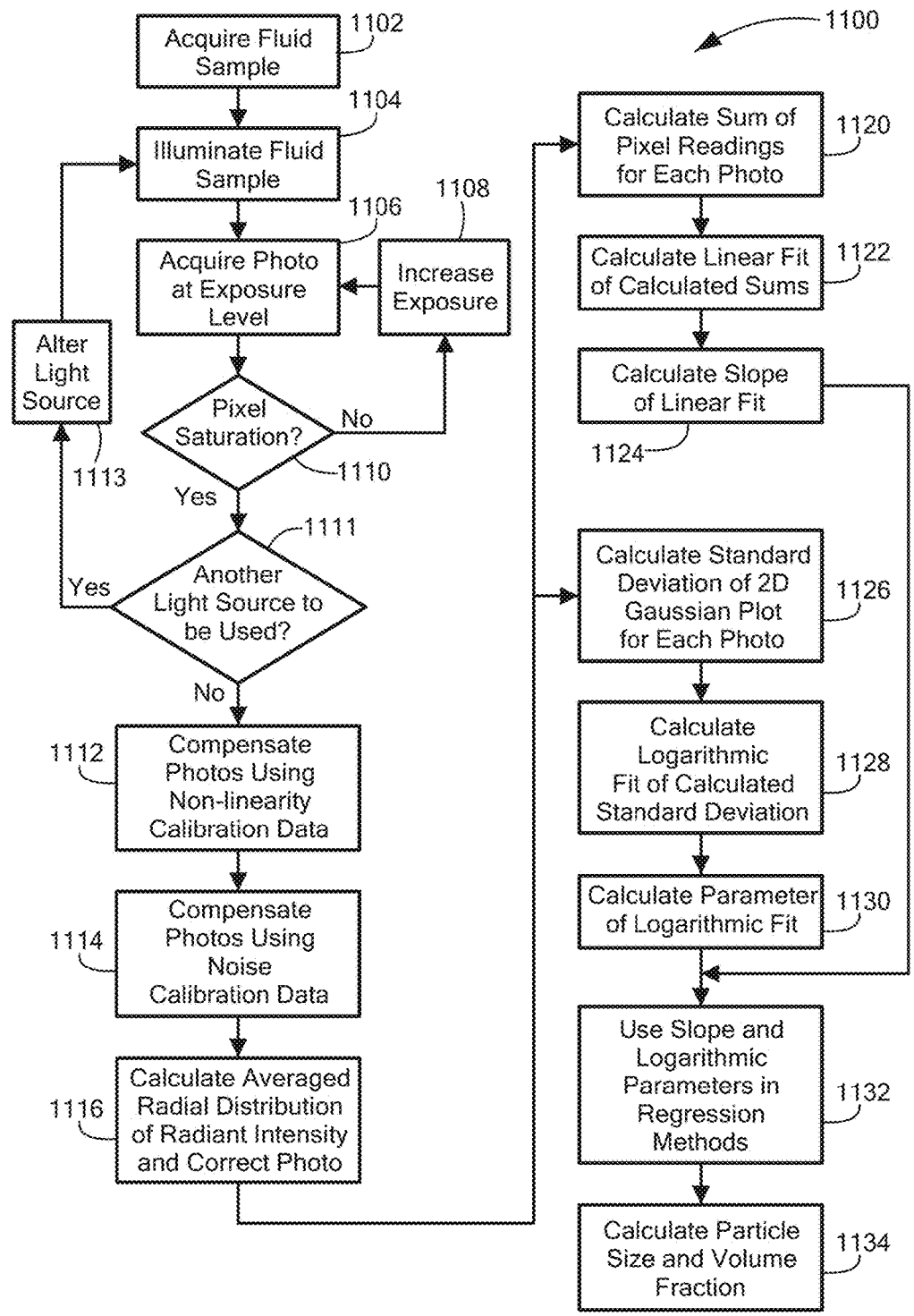
FIG. 11 is a flowchart of a process for analyzing a fluid.

FIG. 11 is a flow diagram showing illustrative processing that can be implemented within the system 100 (FIG. 1). Rectangular elements (typified by element 1102 in FIG. 11), denoted as "processing blocks," represent computer software instructions or groups of instructions. Diamond shaped elements (typified by element 1110 in FIG. 11), denoted as "decision blocks," represent computer software instructions, or groups of instructions, which affect the execution of the computer software instructions represented by the processing blocks. Alternatively, the processing and decision blocks may represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated, the particular sequence of blocks described is illustrative only and can be varied without departing from the spirit of the concepts, structures, and techniques described. Thus, unless otherwise stated the blocks described below are unordered meaning that, when possible, the functions represented by the blocks can be performed in any convenient or desirable order.

Referring now to FIG. 11, an illustrative process 1100 for analyzing a fluid sample begins in processing block 1102 by acquiring a fluid sample. The fluid sample may be acquired, for example, by pumping a fluid sample into a fluid chamber (e.g., such as the chamber described in housing 102 in FIG. 1). The fluid is then illuminated by a light source as shown in processing block 1104. This allows light from light source 114 to be transmitted through and scattered by the fluid sample.

Blocks 1104-1111 and 1113 implement a nested loop in which one or a series of images are captured. The inner loop (comprising blocks 1106, 1108, and 1110) captures a series of photos at different exposure levels (i.e. at different integration times). The outer loop (comprising blocks 1104, 1111, and 1113) alters the light source.

In processing block 1106, an image (e.g. a photo) of the illuminated fluid is captured. If, in decision block 1110, it is determined that the image is not saturated, then processing proceeds to processing block 1108 where the exposure is increased and another photo is acquired as shown in processing block 1106. If, in decision block 1110, it is determined that the exposure is at saturation, the process continues to decision block 1111.

Once a series of photos is captured, it is determined, in block 1111, whether another light source is to be used. If so, the light source is altered in processing block 1113 and the fluid sample is illuminated by the new light source in processing block 1104. With the new light source active, a series of photos may be captured, as described above, in blocks 1106, 1108, and 1110. If the light source is not to be altered, the process continues to processing block 1112.

In processing blocks 1112 and 1114, compensation for non-linearity and noise as described above is performed. In an embodiment, the processing of blocks 1112 and 1114 are performed only once during calibration of the system. In other embodiments, the processing of blocks 1112 and 1114 are performed during each operation of the system.

In processing block 1116, a calculation of the radial distribution intensity of photos is made, (e.g., as described above with regard to FIG. 8). For example, as described above, processor 126 (FIG. 1) may aggregate and average the intensity data of pixels in the captured image. After processing block 1116, the process continues to processing blocks 1120 and 1126.

In processing block 1120, a sum of pixel readings for each photo is made and, in processing block 1122, a linear fit of the calculated sums is made. In processing block 1124, the slope of the linear fit may be calculated and used to determine a particle size of the sample fluid.

In processing block 1126, a standard deviation of the Gaussian plot for each photo is computed. Processor 126 calculates a logarithmic fit of the standard deviation in processing block 1128. In processing block 1130, the logarithmic parameter of the logarithmic fit is calculated.

In processing block 1132, the calculated slope (from processing block 1124) and the calculated logarithmic parameter (from processing block 1130) are used in regression methods. Using the regression methods, a particle size and volume fraction of the fluid sample are calculated in processing block 1134.

Figure 12:
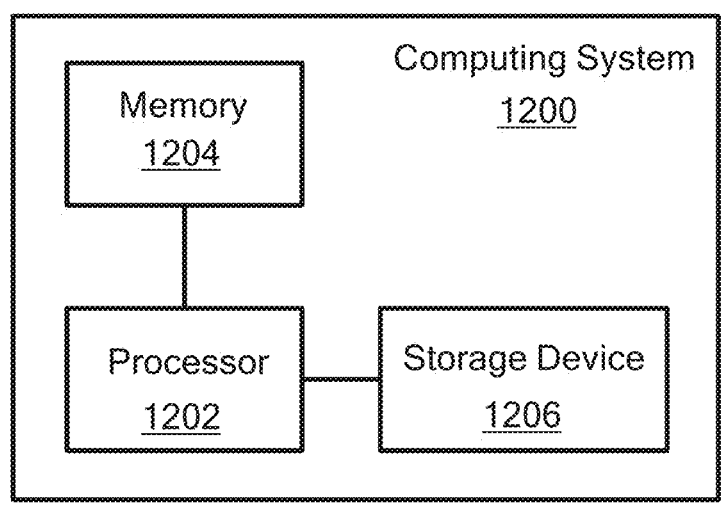
FIG. 12 is a block diagram of a processor suitable for analyzing a fluid in accordance with the concepts described in conjunction with FIGS. 1-11.

FIG. 12 shows an illustrative computing system 1200 that can execute software. System 1200 may be the same as or similar to, or may include, processor 126. System 1200 includes a processor 1202 (which may be the same as or similar to processor 126), a random access memory (RAM) 1204, and a storage device 1206, which may be a hard drive, a CD, a DVD, a flash drive, or any other type of non-volatile memory. Software instructions may be stored in RAM 1204 and/or storage device 1206. Processor 1202 may be coupled to storage device 1206 and/or RAM 1204 so that processor 1202 can read the software instructions. As processor 1202 reads the software instructions, the software instructions may cause processor 1202 to perform operations, as described above, for computing the position of a magnetic target. Although not shown, processor 1202 and/or system 1200 may include other inputs and outputs, such as inputs for receiving the signals from the sensing elements, GPIO, power inputs, or other interfaces such as USB, SATA, HDMI, and the like. Computing system 1200 may perform some or all of the processes, methods, calculations, etc. described above with respect to analysis of a sample fluid.

Having described preferred embodiments, which serve to illustrate various concepts, structures and techniques, which are the subject of this patent, it will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims. All references cited above are hereby incorporated by reference in their entirety.

The invention claimed is:
1. A system for analyzing fluid comprising:
   a housing having first and second opposing surfaces spaced to form a fluid chamber;
   a light source disposed to direct light at the first surface of the housing;
   a digital imaging circuit disposed to detect light at the second surface of the housing, said digital imaging circuit having a pixel array configured to capture one or more digital images of an illuminated fluid; and
   a processor configured to:
      capture multiple digital images of the light through the fluid at different camera exposure levels;
      calculate a net radiant energy value at each of a plurality of different integration times within at least two images;
      calculate a slope of the net radiant energy values with respect to integration time in a selected image; and
      determine a particle size distribution and volume fraction of particles within the fluid based on the calculated slope.
2. The system of claim 1 wherein the processor is further configured to determine a property of the fluid based on a predetermined range of particle sizes.

3. The system of claim 2 wherein the fluid is milk and the property is a fat and/or protein content.

4. The system of claim 1 wherein the opposing surfaces are clear.

5. The system of claim 1 wherein at least one of the opposing surfaces comprises a light filter.

6. The system of claim 1 wherein the light source comprises one or more of a laser diode, an LED, an incandescent lamp, and/or a halogen/mercury lamp.

7. The system of claim 1 wherein the system includes a lens positioned to focus an image of the light on the pixel array.

8. The system of claim 1 wherein the processor is further configured to filter noise from the digital images.

9. The system of claim 8 wherein the processor is configured to filter the noise by averaging pixel readings at each radial distance from a center of the digital images.

10. The system of claim 1 wherein calculating the net radiant energy value includes performing a sum or integration of pixel readings of the digital images.

11. The system of claim 1 wherein the processor is configured to calculate a logarithmic parameter of the digital images.

12. The system of claim 11 wherein the processor is configured to calculate the logarithmic parameter by calculating a standard deviation of pixel readings in each digital image and performing a best logarithmic fit of the standard deviation values with respect to integration time.

13. The system of claim 1 wherein the processor is configured to control the light source.

14. The system of claim 1 wherein light source comprises multiple light sources and the processor is configured to capture the digital images illuminated by one or more of the multiple light sources.

15. The system of claim 1 wherein the processor is further configured to perform regression analysis using one or more regression models and the calculated slope to compute particle size distribution and volume fraction of the fluid sample.

16. The system of claim 15 wherein the processor is configured to compute a logarithmic parameter for use in the one or more regression models.

17. A method for analyzing a fluid comprising:
illuminating a fluid sample with a light source;
capturing, with a digital camera circuit, a plurality of digital images of the illuminated fluid sample at different camera exposure levels;
calculating, with a processing circuit, a net radiant energy value at each of a plurality of different integration times within at least two images;
calculating, with the processing circuit, a slope of the net radiant energy values with respect to integration time in a selected image;
determining a size distribution of particles within the fluid sample based on the calculated slope.

18. The method of claim 17 further comprising determining a property of a fluid based on the predetermined particle size.

19. The method of claim 18 wherein the fluid is milk and the property is a fat and/or protein content.

20. The method of claim 17 further comprising pumping the fluid sample into a housing having a chamber between two opposing, clear surfaces.

21. The method of claim 20 wherein at least one of the surfaces comprises a light filter.

22. The method of claim 17 wherein the light source comprises one or more of a laser diode, an LED, an incandescent lamp, and/or a halogen/mercury lamp.

23. The method of claim 17 further comprising positioning a lens to focus an image of fluid on the pixel array.

24. The method of claim 17 further comprising filtering noise from the digital images.

25. The method of claim 24 wherein filtering the noise includes averaging pixel readings at each radial distance from a center of the digital images.

26. The method of claim 17 wherein calculating the net radiant energy value includes performing a sum or integration of pixel readings of the digital images.

* * * * *